(12) United States Patent
Caylor, III

(10) Patent No.: US 9,295,555 B2
(45) Date of Patent: Mar. 29, 2016

(54) ACETABULAR CUP HAVING A WIRELESS COMMUNICATION DEVICE

(71) Applicant: DePuy Synthes Products, Inc., Raynham, MA (US)

(72) Inventor: Edward J. Caylor, III, Fort Wayne, IN (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 0 days.

(21) Appl. No.: 14/153,700

(22) Filed: Jan. 13, 2014

(65) Prior Publication Data

US 2014/0124129 A1  May 8, 2014

Related U.S. Application Data

(62) Division of application No. 11/537,359, filed on Sep. 29, 2006, now Pat. No. 8,641,771.

(51) Int. Cl.
*A61F 2/34* (2006.01)
*A61B 5/07* (2006.01)
(Continued)

(52) U.S. Cl.
CPC . *A61F 2/34* (2013.01); *A61B 5/076* (2013.01); *A61B 5/4528* (2013.01); *A61B 5/6846* (2013.01); *A61B 5/03* (2013.01); *A61B 2560/0219* (2013.01); *A61F 2/3094* (2013.01); *A61F 2/30771* (2013.01); *A61F 2002/302* (2013.01); *A61F 2002/3067* (2013.01); *A61F 2002/3071* (2013.01); *A61F 2002/30153* (2013.01); *A61F 2002/30289* (2013.01); *A61F 2002/30367* (2013.01); *A61F 2002/30403* (2013.01); *A61F 2002/30448* (2013.01);

(Continued)

(58) Field of Classification Search
CPC ............... A61F 2/30; A61F 2/34; A61B 5/05
USPC .................... 623/18.11–19.12, 22.11–23.46; 600/424
See application file for complete search history.

(56) References Cited

U.S. PATENT DOCUMENTS 5,300,120 A    4/1994  Knapp et al.
5,423,334 A    6/1995  Jordan
(Continued)

FOREIGN PATENT DOCUMENTS

WO   20050039440   5/2005
WO   20050084544   9/2005
WO   20050087125   9/2005

OTHER PUBLICATIONS

European Search Report; European Patent Application No. 10165631.2-2310; Aug. 3, 2010; 5 pages.
(Continued)

*Primary Examiner* — Yashita Sharma
(74) *Attorney, Agent, or Firm* — Barnes & Thornburg, LLP

(57) ABSTRACT

A orthopaedic implant comprises an acetabular cup and a wireless communication device. The wireless communication device is coupled to a rim surface of the acetabular cup. In one embodiment, a recess is defined in the rim surface and the wireless communication device is positioned therein. In another embodiment, the wireless communication device is positioned in an annular ring formed of a biocompatible material. The annular ring is coupled to the rim surface of the acetabular cup. The wireless communication device may be, for example, a radio frequency identification (RFID) tag or device.

5 Claims, 9 Drawing Sheets

(51) Int. Cl.
*A61B 5/00* (2006.01)
*A61B 5/03* (2006.01)
*A61F 2/30* (2006.01)
*A61F 2/32* (2006.01)

(52) U.S. Cl.
CPC .................. *A61F2002/30449* (2013.01); *A61F 2002/30589* (2013.01); *A61F 2002/30822* (2013.01); *A61F 2002/30825* (2013.01); *A61F 2002/30957* (2013.01); *A61F 2002/3241* (2013.01); *A61F 2220/005* (2013.01); *A61F 2220/0025* (2013.01); *A61F 2220/0033* (2013.01); *A61F 2230/0019* (2013.01); *A61F 2230/0065* (2013.01); *A61F 2230/0091* (2013.01); *A61F 2250/0002* (2013.01); *A61F 2250/0085* (2013.01); *A61F 2310/00023* (2013.01); *Y10T 156/1064* (2015.01)

(56) References Cited

U.S. PATENT DOCUMENTS

| | | | |
|---|---|---|---|
| 6,366,206 | B1 | 4/2002 | Ishikawa et al. |
| 2003/0097178 | A1 | 5/2003 | Roberson et al. |
| 2003/0153981 | A1 | 8/2003 | Wang et al. |
| 2005/0010301 | A1 | 1/2005 | Disilvestro et al. |
| 2005/0027192 | A1 | 2/2005 | Govari et al. |
| 2006/0142656 | A1 | 6/2006 | Malackowski et al. |
| 2007/0238992 | A1 | 10/2007 | Donofrio et al. |

OTHER PUBLICATIONS

European Search Report for European Application No. 07253839.0-2310, Jan. 7, 2008, 7 pgs.

"Radio Frequency Identification" Wikipedia, http://en.wikipedia.org/wiki/RFID, 12 pages; Sep. 26, 2006.

ACETABULAR CUP HAVING A WIRELESS COMMUNICATION DEVICE

This application is a divisional application of U.S. patent application Ser. No. 11/537,359, which was filed on Sep. 29, 2006 and is expressly incorporated herein by reference.

TECHNICAL FIELD

The present disclosure relates generally to acetabular cups, and particularly, to acetabular cups having a wireless communication device coupled thereto.

BACKGROUND

Orthopaedic implants or prostheses are implanted in patients by orthopaedic surgeons to, for example, correct or otherwise alleviate bone and/or soft tissue loss, trauma damage, and/or deformation of the bone(s) of the patients. One orthopaedic surgical procedure in which an orthopaedic implant is used is a partial or total hip replacement procedure. One of the implant components used in such a surgical procedure is an acetabular cup, which is secured to the acetabulum of the patient. The acetabular cup replaces the natural bearing surface of the acetabulum and provides a new bearing surface for the head portion of the patient's femur or femoral implant component.

Radio frequency identification (RFID) tags are devices typically used to track items such as, for example, items to be purchased or placed into inventory. An RFID tag typically includes a transponder configured to transmit data, such as a serial number associated with the RFID tag, in response to an integrator signal. An RFID reader is typically used to transmit the integrator signal and receive the data from the RFID tag.

SUMMARY

According to one aspect, an acetabular cup includes an outer surface, an inner surface, and a rim surface defined between the outer surface and the inner surface. The outer surface may be configured to confront a portion of an acetabulum of a patient when the acetabular cup is implanted in the patient. The inner surface may form an inner cavity configured to receive a bearing insert. The rim surface may have a recess defined therein. The recess may be, for example, an annular recess. A wireless communication device may be positioned in the recess of the rim surface. The wireless communication device may be secured in the recess via use of a biocompatible compound such as, for example, bone cement. The wireless communication device may be, for example, a radio frequency identification (RFID) tag or device. In some embodiments, the wireless communication device may include a transponder circuit and an antenna. The antenna may be, for example, a coil antenna. The transponder circuit may be configured to transmit identification data associated with the acetabular cup. The transponder circuit may transmit the identification data in response to an interrogation signal received via the antenna. The wireless communication device may be configured to transmit data, such as the identification data, using a frequency in the range of 30 kilohertz to 30 megahertz. The acetabular cup may also include a sensor electrically coupled to the wireless communication device. The sensor may be configured to generate sensor data. In such embodiments, the wireless communication device may be configured to transmit the sensor data.

According to another aspect, a method for fabricating an orthopaedic implant may include forming a recess in a rim surface of an acetabular cup. The recess may be, for example, an annular recess defined in the rim surface. The method may also include positioning a wireless communication device, such as a radio frequency identification (RFID) tag, in the recess. Additionally, the method may include securing the wireless communication device in the recess using a biocompatible compound. For example, the wireless communication device may be secured in the recess by depositing an amount of bone cement into the recess.

According to a further aspect, an orthopaedic implant may include an acetabular cup. The acetabular cup may have an outer surface, an inner surface, and a rim surface defined between the outer surface and the inner surface. The orthopaedic implant may also include an annular ring formed from a biocompatible material. The annular ring may be coupled to the rim surface of the acetabular cup. In some embodiments, the annular ring includes a bottom surface that is in registry with the rim surface of the acetabular cup when the annular ring is coupled thereto. The annular ring may be formed from any biocompatible material. Additionally, the annular ring may be formed from a dielectric material. The orthopaedic implant may further include a wireless communication device positioned in the annular ring. The wireless communication device may be, for example, a radio frequency identification (RFID) tag. In some embodiments, the wireless communication device may include a transponder circuit and an antenna. The antenna may be, for example, a dipole antenna such as a meandering dipole antenna. The transponder circuit may be configured to transmit identification data associated with the acetabular cup. The transponder circuit may transmit the identification data in response to an interrogation signal received via the antenna. The wireless communication device may be configured to transmit data, such as the identification data, using a frequency in the range of 30 megahertz to 3,000 megahertz. The acetabular cup may also include a sensor electrically coupled to the wireless communication device. The sensor may be configured to generate sensor data. In such embodiments, the wireless communication device may be configured to transmit the sensor data.

According to yet another aspect, a method for fabricating an orthopaedic implant may include forming an annular ring from a biocompatible material. The annular ring may have a wireless communication device positioned therein. For example, the annular ring may be formed by molding the biocompatible material around the wireless communication device. The wireless communication device may be, for example, a radio frequency identification (RFID) tag. The method may also include securing the annular ring to a rim surface of an acetabular cup. The annular ring may have a bottom surface that is in registry with the rim surface of the acetabular cup when coupled thereto.

BRIEF DESCRIPTION OF THE DRAWINGS

The detailed description particularly refers to the following figures, in which.

DETAILED DESCRIPTION OF THE DRAWINGS

Figure 1:
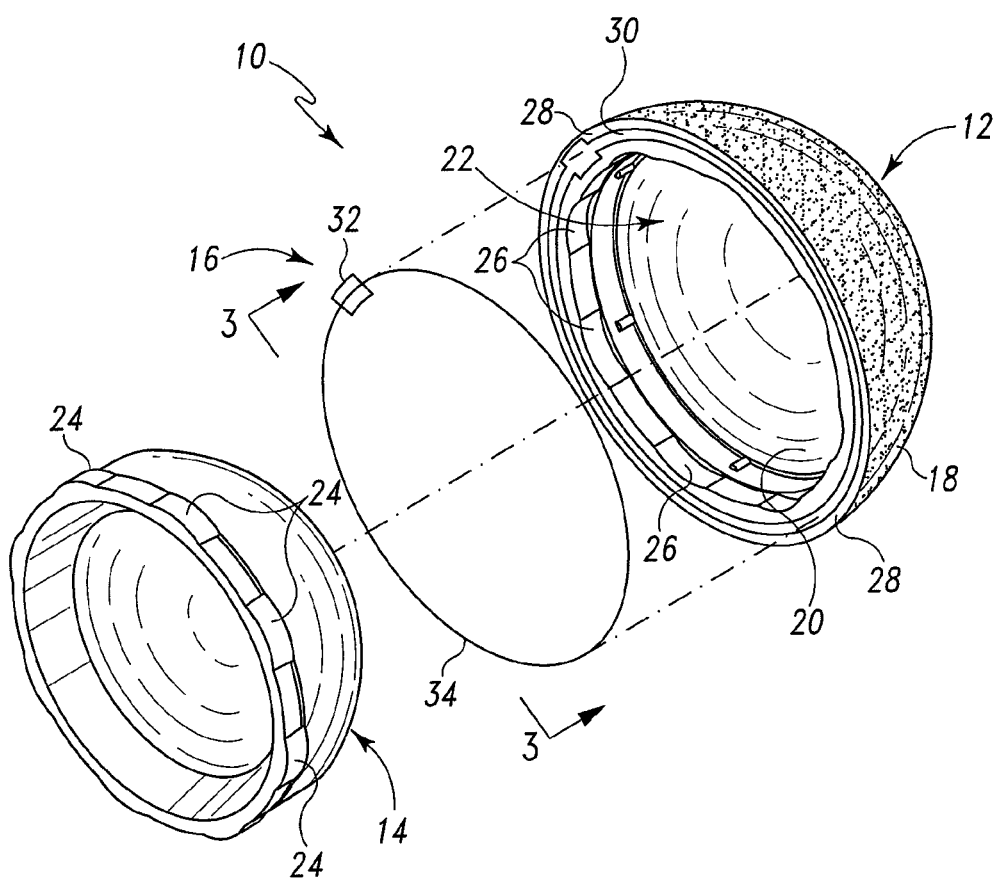
FIG. 1 is an exploded perspective view of one embodiment of an orthopaedic implant having a wireless communication device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an orthopaedic implant 10 includes an acetabular cup 12, a bearing insert 14, and a wireless communication device 16. The acetabular cup 12 includes an outer surface 18 and an inner surface 20. The acetabular cup 12 may be formed from any suitable material capable of being secured to the acetabulum of a patient and supporting a natural or artificial head portion of a femur of the patient. For example, the acetabular cup 12 may be formed from a titanium alloy. In some embodiments, the outer surface 18 of the acetabular cup 12 may have a textured or porous surface. Such a textured or porous surface may enhance bone ingrowth when the acetabular cup 12 is secured to the acetabulum. Such bone ingrowth may facilitate long-term attachment of the acetabular cup 12 to the acetabulum.

The inner surface 20 of the acetabular cup 12 is concave in shape and forms an inner cavity 22. The inner cavity 22 is shaped to receive the bearing insert 14. The bearing insert 14 provides an artificial surface for a natural or artificial head portion of the femur of the patient and may be formed from any material suitable for such purpose. For example, the bearing insert 14 may be formed from a polymeric material such as polyethylene or ultra-high molecular weight polypropylene (UHMWPE). In some embodiments, the bearing insert 14 may include a number of keying tabs 24 that are received by a number of keying slots 26 defined in the inner surface 18 of the acetabular cup 12. When the bearing insert 14 is positioned in the inner cavity 22 of the acetabular cup 12, the keying slots 26 receive the keying tabs 24 and thereby reduce the likelihood of rotation of the bearing insert 14 relative to the acetabular cup 12. As such, the acetabular cup 12 and the bearing insert 14 cooperate to provide an artificial bearing surface on which a natural or artificial head portion of a femur of a patient may bear.

The acetabular cup 12 includes a rim surface 28 defined between the outer surface 18 and the inner surface 20. The rim surface 28 is substantially planar and includes a recess 30 defined therein. The recess 30 is configured to receive the wireless communication device 16. For example, the recess 28 may be formed to have a length, width, and depth large enough such that the wireless communication device 16 does not extend pass the rim surface 28 when positioned in the recess 30. As such, the particular configuration of the recess 30 may depend upon the type, size, and/or number of components of the wireless communication device 16. In the illustrative embodiment of FIG. 1, the recess 30 has a substantially annular top profile and extends the length of the rim surface 28. However, in other embodiments, the recess may have any shape configured to receive the wireless communication device. For example, in some embodiments, the recess 30 may be formed so as to not extend the complete length of the rim surface 28.

Figure 9:
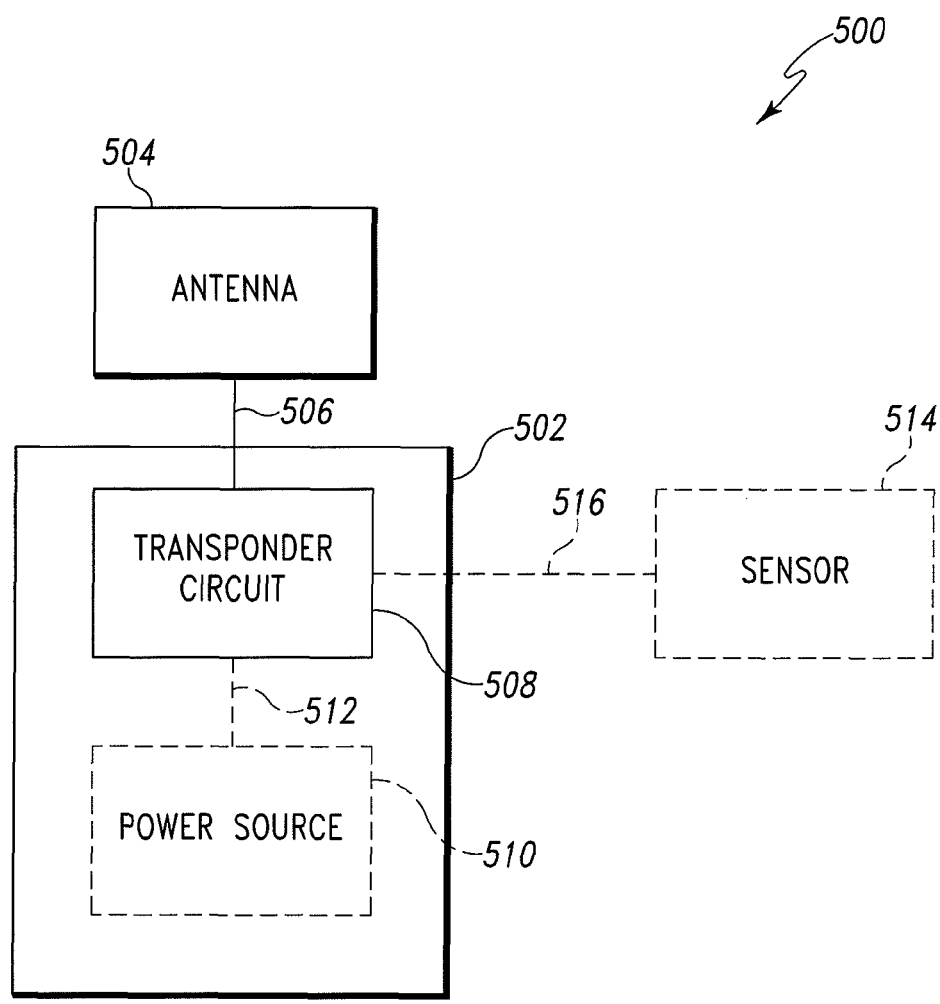
FIG. 9 is a block diagram of one embodiment of the wireless communication device of FIGS. 1 and 5.

The wireless communication device 16 may be embodied as any type of device capable of transmitting and/or receiving data via a wireless communication connection. In one particular embodiment, the wireless communication device 16 is embodied as a radio frequency identification (RFID) tag or device. For example, as illustrated in FIG. 9, the wireless communication device 16 may be embodied as an RFID device 500 having a communication circuit 502 and an antenna 504. The communication circuit 502 is coupled to the antenna 504 via a number of communication links 506. The communication link 506 may be embodied as any type of communication links capable of facilitating electrical communication between the transponder circuit 508 and the antenna 504. For example, the communication link 506 may be embodied as any number of wires, cables, printed circuit board (PCB) traces, vias, fiber optic cables, and/or the like.

The RFID device 500 may be a passive RFID device or an active RFID device. In embodiments wherein the RFID device 500 is embodied as a passive RFID device, the communication circuit 502 is embodied as, or otherwise includes, a transponder circuit 508. The transponder circuit 508 is configured to transmit a data signal in response to an interrogation signal received via the antenna 504. For example, the transponder circuit 508 may be configured to transmit the data signal by backscattering the carrier signal of the interrogation signal. The data signal may be embodied as or include any type of data such as, for example, an identification number or other data associated with the RFID device 500. The interrogation signal may be generated by, for example, an RFID reader (not shown) or the like and, in some embodiments, provides a power signal to the transponder circuit 508 or portion thereof.

In embodiments wherein the RFID device 500 is embodied as a passive RFID device, the antenna 504 may be embodied as any type of antenna capable of receiving the interrogation signal and transmitting the data signal. The particular type of antenna used may also depend upon the predetermined frequency used by the RFID device 500. For example, in some embodiments the RFID device 500 may be configured to transmit the data signal using a frequency in the low frequency (LF) or high frequency (HF) range (e.g., a frequency in the range of about 30 kilohertz to about 30 megahertz). In such embodiments, the antenna 504 may be embodied as a coil antenna having one or more turns. Alternatively, in other embodiments, the RFID device 500 may be configured to transmit the data signal using a frequency in the very high frequency (VHF) or ultra high frequency (UHF) range (e.g., a frequency in the range of about 30 megahertz to about 3,000 megahertz). In such embodiments, the antenna 504 may be embodied as a dipole antenna such as, for example, a straight or meandering line dipole antenna.

In embodiments wherein the RFID device 500 is embodied as an active RFID device, the communication circuit 502 may also include a power source 510. In such embodiments, the power source 510 is coupled to the transponder circuit 508 via a number of communication links 512. The communication link 512 may be embodied as any type of communication link capable of facilitating electrical communication between the transponder circuit 508 and the power source 510. For example, the communication link 512 may be embodied as any number of wires, cables, printed circuit board (PCB) traces, vias, fiber optic cables, and/or the like.

The power source 510 may be embodied as any type of power source capable of providing power to the transponder circuit 508. For example, in one embodiment, the power source 510 may be embodied as a number of rechargeable batteries. Additionally or alternatively, the power source 510 may be embodied as or otherwise include a secondary coil configured to be inductively coupled to a primary coil positioned outside of the patient's body. When inductively coupled, the primary coil may generate a current in the secondary coil to thereby provide a power signal to the transponder circuit 508 and/or recharge a number of rechargeable batteries or other power storage devices such as a bank of capacitors or the like.

In some embodiments, one or more implant sensors 514 may be communicatively coupled to the communication circuit 502 (e.g., to the transponder circuit 508). The implant sensor(s) 514 may be embodied as any type of sensor capable of generating implant sensor data of a parameter of interest. For example, the implant sensor 514 may be embodied as a pressure sensor, a load sensor, a temperature sensor, a hall-effect sensor, or the like. It should be appreciated that although only a single sensor 514 is illustrated in FIG. 9, in other embodiments, any number of similar and/or different implant sensors may be used. In addition, the implant sensor(s) 514 may be coupled to the orthopaedic implant 10 (e.g., to the outer surface 18 of the acetabular cup 12) or positioned remote therefrom.

Referring now back to FIG. 1, the illustrative wireless communication device 16 includes a communication circuit 32 and an antenna 34. In embodiments wherein the wireless communication device 16 is embodied as an RFID device, the communication circuit 32 may be substantially similar to the communication device 502 illustrated in and described above in regard to FIG. 9. Additionally, the antenna 34 may be substantially similar to the antenna 504. In one particular embodiment, the wireless communication device 16 is configured to transmit data, such as identification data associated with the orthopaedic implant 10 and/or implant sensor data, using a predetermined frequency in the low frequency (LF) or high frequency (HF) range. For example, the wireless communication device 16 may use a frequency in the range of about 30 kilohertz to about 30 megahertz. In such embodiments, the antenna 34 may be embodied as a coil antenna having one or more turns. However, it should be appreciated that in other embodiments other types of antennas may be used.

Figure 2:
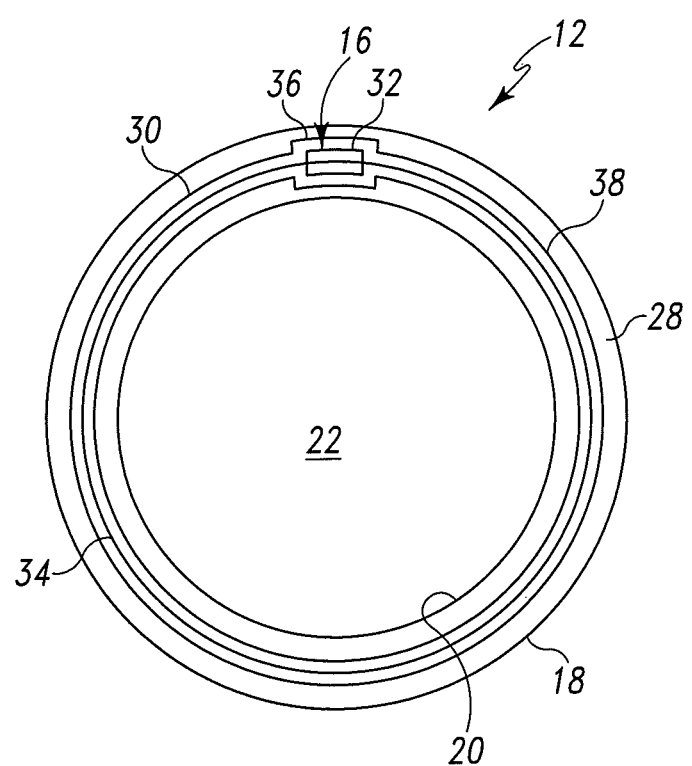
FIG. 2 is a front elevation view of an acetabular cup of the orthopaedic implant of FIG. 1.
Figure 3:
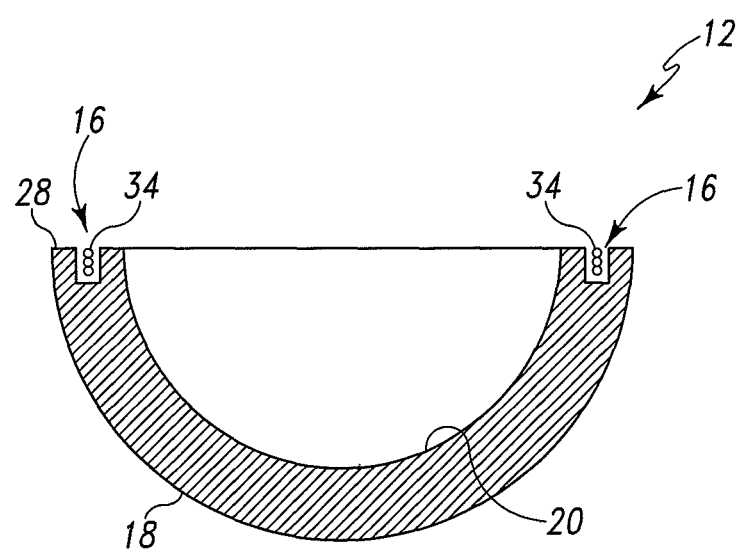
FIG. 3 is a cross-sectional view of the acetabular cup of the orthopaedic implant of FIG. 1 taken generally along the cross-section line 3-3.

As illustrated in FIGS. 2 and 3, the wireless communication device 16 is positioned in the recess 30 of the rim surface 28. To facilitate the positioning of the wireless communication device 16, the recess 30 includes a circuit-receiving recess portion 36 and an antenna-receiving recess portion 38. The circuit-receiving recess portion 36 is configured to receive the communication circuit 32 of the wireless communication device 16. For example, the circuit-receiving recess portion 36 may have a size and shape based on the size and shape of the communication circuit 32. In one particular embodiment as illustrated in FIG. 2, the circuit-receiving recess portion 36 has a substantially rectangular top-profile configured to receive a rectangular shaped communication circuit 32.

Similarly, the antenna-receiving recess portion 38 is configured to receive the antenna 34 of the wireless communication device 16. As such, the antenna-receiving recess portion 38 may have a size and shape based on the size and shape of the antenna 34. For example, in embodiments wherein the antenna 34 is embodied as a coil antenna, the antenna receiving recess portion 38 is embodied as an annular shaped channel recess that extends the length of rim surface 28. As illustrated in FIG. 3, when the antenna 34 of the wireless communication device 16 is positioned in the antenna-receiving recess portion 38, the individual turns of the antenna 34 may be stacked on top of each other.

Once the wireless communication device 16 is positioned in the recess 30 (e.g., the communication circuit 32 is positioned in the circuit-receiving recess portion 36 and the antenna 34 is positioned in the antenna-receiving portion 38), the device 16 may be secured in recess 30. In one embodiment, a suitable adhesive may be used to secure the wireless communication device 16 in the recess 30. For example, a biocompatible compound may be used such that the adhesive does not adversely affect the surrounding tissue or bone of the patient. Additionally, in some embodiments, the recess 30 may be sealed once the wireless communication device 16 has been positioned in the recess 30. The recess 30 may be sealed using any suitable biocompatible sealant or adhesive. In some embodiments, the wireless communication device 16 is secured in a position in the recess 30 and the recess 30 is sealed using the same sealant or adhesive. For example, in one particular embodiment, the wireless communication device 16 is secured in a position in the recess 30 by filling, or substantially filing, the recess 30 with bone cement.

Figure 4:
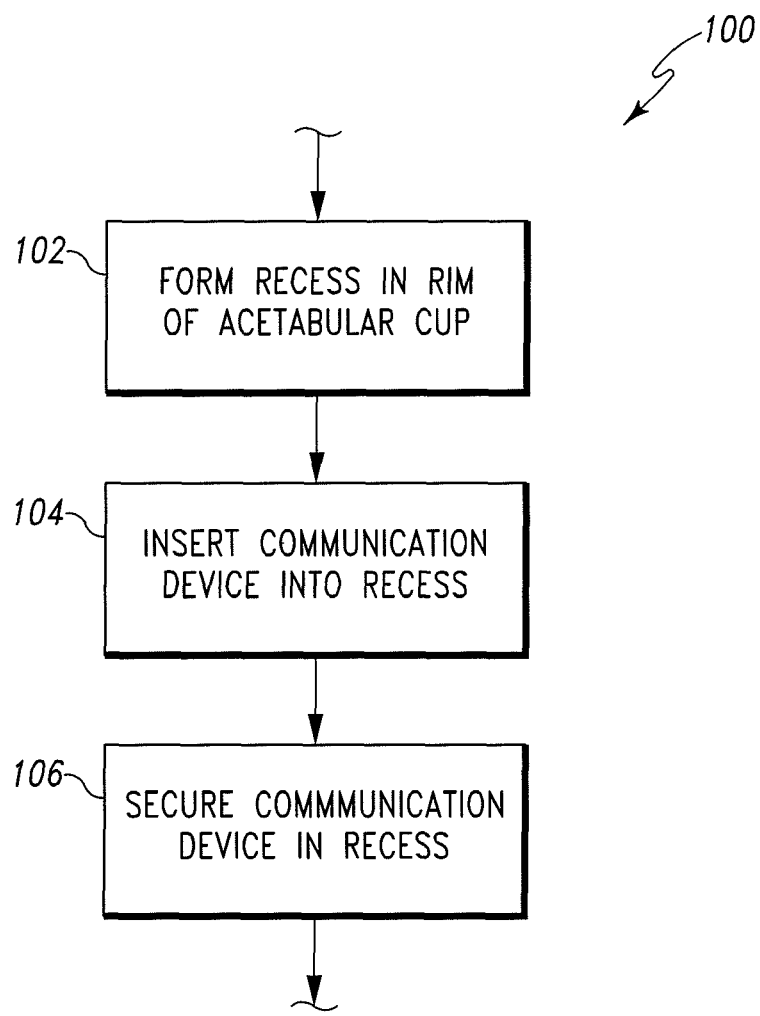
FIG. 4 is a simplified flowchart of an algorithm for fabricating the acetabular cup of the orthopaedic implant of FIG. 1.

Referring now to FIG. 4, an algorithm 100 for fabricating the orthopaedic implant 10 begins with a process step 102. In process step 102, the recess 30 is formed in the rim surface 28 of the acetabular cup 12. That is, the circuit-receiving recess portion 36 and the antenna-receiving recess portion 38 are formed in the rim surface 28. As discussed above in regard to FIGS. 2 and 3, the circuit-receiving recess portion 36 and the antenna-receiving recess portion 38 may be formed to have a shape and size based on the shape and size of the communication circuit 32 and the antenna 34 of the wireless communication device 16, respectively. The recess 30 may be formed in the rim surface 28 by, for example, milling the rim surface 28. Alternatively, the acetabular cup 12 may be formed to include the recess 30 defined in the rim surface 28. For example, depending on the material from which the acetabular cup 12 is formed, the acetabular cup 12 may be molded to include the recess 30 defined in the rim surface 28.

Once the recess 30 has been defined in the rim surface 28 of the acetabular cup 12, the wireless communication device 16 is positioned in the recess 30 in process step 104. To do so, the communication circuit 32 is positioned in the circuit-receiving recess portion 36 of the recess 30. Similarly, the antenna 34 is positioned in the antenna-receiving portion 38. In some embodiments, the wireless communication device 16 may be so positioned and/or the recess 30 is formed such that no portion of the wireless communication device 16 extends past the rim surface 28 of the acetabular cup 12.

Once the wireless communication device 16 has been positioned in the recess 30, the wireless communication device 16 is secured in the recess 30 in process step 106. As discussed above in regard to FIGS. 2 and 3, the wireless communication device 16 may be secured in the recess 30 using a biocompatible adhesive. Additionally, in some embodiments, the recess 30 may be sealed once the wireless communication device 16 has been positioned in the recess 30 using a suitable biocompatible sealant or adhesive. For example, in one particular embodiment, the wireless communication device 16 is secured in the recess 30 by filling, or substantially filing, the recess 30 with bone cement.

Figure 5:
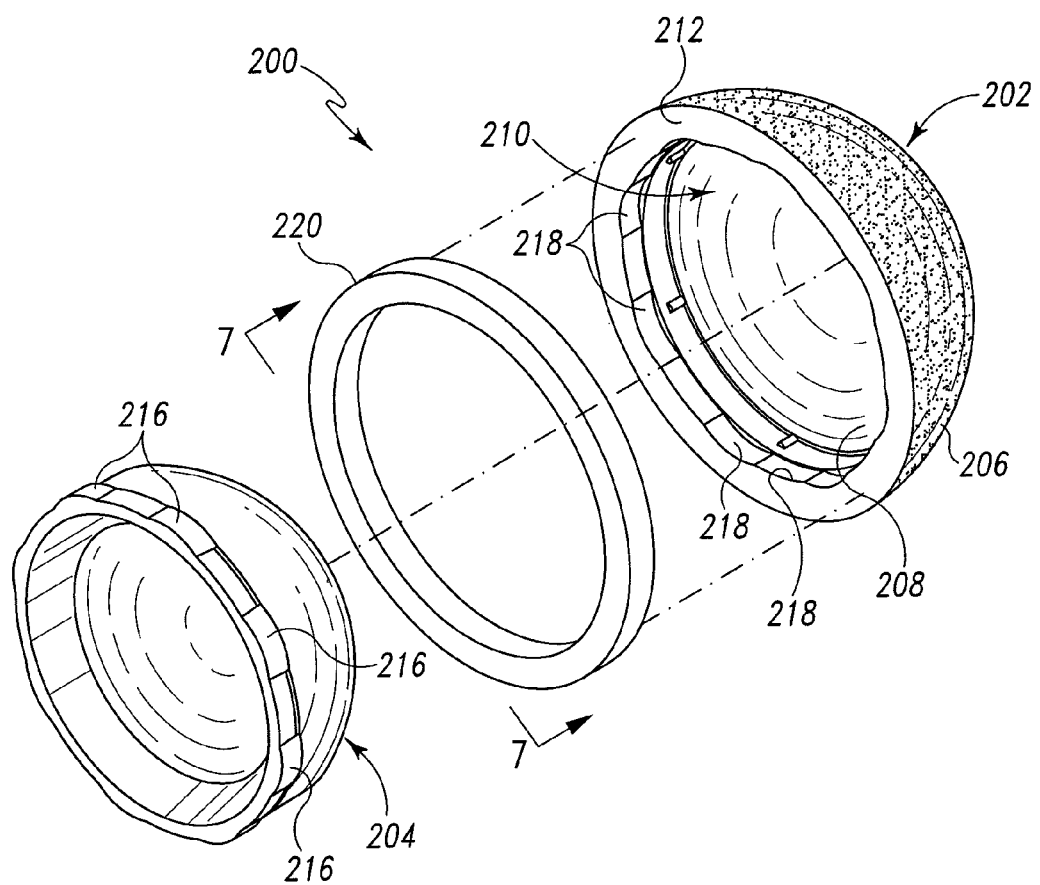
FIG. 5 is an exploded perspective view of another embodiment of an orthopaedic implant having a wireless communication device.
Figure 6:
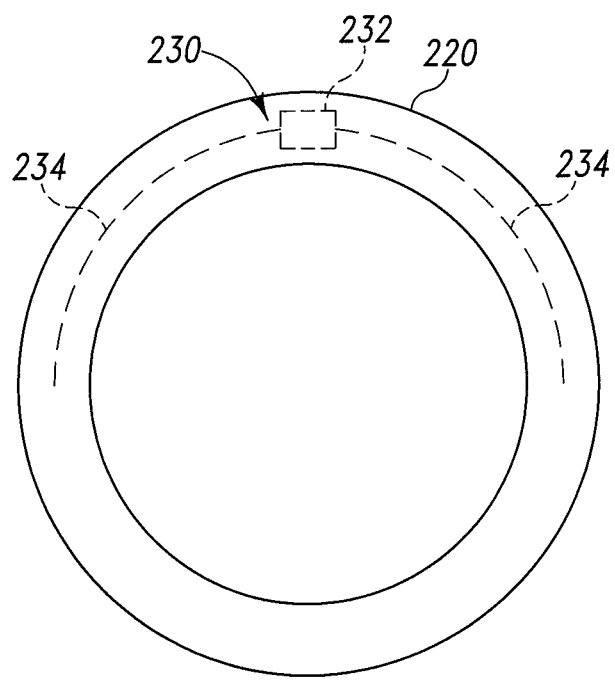
FIG. 6 is a front elevation view of an annular ring coupled to an acetabular cup of the orthopaedic implant of FIG. 5.
Figure 7:
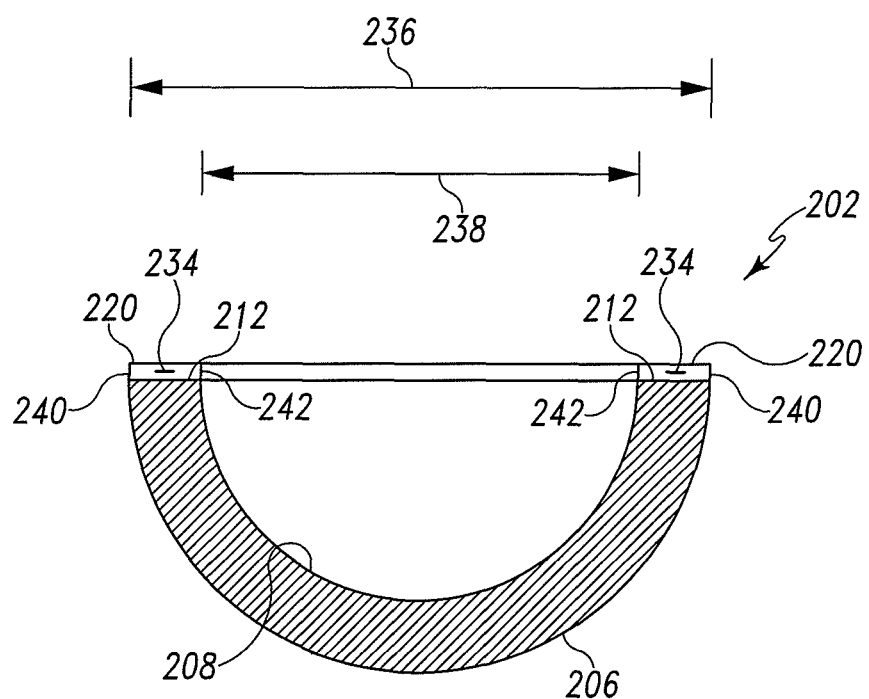
FIG. 7 is a cross-sectional view of the acetabular cup and annular ring of the orthopaedic implant of FIG. 1 taken generally along the cross-section line 7-7.

Referring now to FIG. 5, in another embodiment, an orthopaedic implant 200 includes an acetabular cup 202, a bearing insert 204, an annular ring 220, and a wireless communication device 230 positioned in the annular ring 200 (see FIGS. 6 and 7). The acetabular cup 202 is similar to the acetabular cup 12 and includes an outer surface 206, and inner surface 208, and a rim surface 212 defined therebetween. The acetabular cup 202 may be formed from any suitable material capable of being secured to the acetabulum of a patient and supporting a natural or artificial head portion of a femur of the patient. For example, the acetabular cup 202 may be formed from a titanium alloy. Similar to the acetabular cup 12, the outer surface 202 of the acetabular cup 202 may have a textured or porous surface in some embodiments.

Additionally, similar to the inner surface 20 of the acetabular cup 12, the inner surface 208 of the acetabular cup 202 is concave in shape and forms an inner cavity 210. The inner cavity 210 is shaped to receive the bearing insert 204. The bearing insert 204 is substantially similar to the bearing insert 14 and provides an artificial surface for a natural or artificial head portion of the femur of the patient. The bearing insert 204 may be formed from any suitable material such as, for example, a polymeric material such as polyethylene or ultra-high molecular weight polypropylene (UHMWPE). As discussed in detail above in regard to the bearing insert 14 illustrated in FIG. 1, the bearing insert 204 may include a number of keying tabs 216 which are received by a number of keying slots 218 defined in the inner surface 208 of the acetabular cup 202 to reduce the likelihood of rotation of the bearing insert 204 relative to the acetabular cup 202.

The annular ring 220 is formed in a size and shape as to be couplable to the rim surface 212 of the acetabular cup 202. The annular ring 220 may be coupled to the rim surface 212 using any suitable biocompatible adhesive. As illustrated in FIGS. 6 and 7, the wireless communication device 230 is positioned in the annular ring 220. The annular ring 220 may be formed from any material that is coupleable to the acetabular cup 202 and that does not overly attenuate the reception and/or transmission of the wireless communication device 230. For example, in embodiments wherein the wireless communication device 230 is embodied as an RFID device such as RFID device 500 illustrated in and described below in regard to FIG. 9, the annular ring 220 is formed from a material that allows the wireless communication device 230 to receive an interrogation signal and transmit data such as identification data associated with the orthopaedic implant 200. For example, the annular ring 220 may be formed from a dielectric material. Additionally, in some embodiments, the annular ring 220 is formed from a polymeric material such as polyethylene or ultra-high molecular weight polypropylene (UHMWPE) similar to the bearing insert 204.

The shape and size of the annular ring 220 may be dependent upon the shape and size of the rim surface 212 and/or the acetabular cup 202. For example, as illustrated in FIG. 5, the annular ring may have a substantially circular top profile in embodiments wherein the rim surface 212 also has a substantially circular top profile. However, in other embodiments, annular rings having other top profile shapes may be used. For example, in some embodiments, the annular ring 220 may have an elliptical shape or the like.

In one particular embodiment, as illustrated in FIG. 7, the annular ring 230 has an outer diameter 236 substantially equal to the outer diameter of the acetabular cup 202 such that an outer sidewall 240 of the annular ring 220 is substantially congruent with the distal end of the outer surface 206 of the acetabular cup 202. In addition, the annular ring 220 has an inner diameter 238 substantially equal to the inner diameter of the acetabular cup 202 such that an inner sidewall 242 of the annular ring 220 is substantially congruent with the distal end of the inner surface 208. That is, the annular ring 220 may be formed to have a shape such that the annular ring 220 is in a registered relationship with the rim surface 212 of the acetabular cup 202 when the annular ring 220 is coupled thereto in some embodiments. Regardless, the annular ring 220 is configured to be coupled to the rim surface 212 of the acetabular cup 202.

The wireless communication device 230 is positioned in the annular ring 220. The wireless communication device 230 may be so positioned by forming the annular ring 220 around the wireless communication device 230. For example, in embodiments, wherein the annular ring 220 is formed from a polymeric material, the annular ring 220 may be molded around the wireless communication device 230. Alternatively, in some embodiments, the annular ring 220 includes an inner chamber in which the wireless communication device 230 is positioned. Regardless, when the annular ring 220 is coupled to the rim surface 212 of the acetabular cup 202, the wireless communication device 230 is positioned on top of the acetabular cup 202 as illustrated in FIG. 7. Such positioning of the wireless communication device 230 may reduce the attenuation of the reception and/or transmission signals of the device 230 due to the acetabular cup 12 and/or bony anatomy of the patient.

The illustrative wireless communication device 230 of FIGS. 6 and 7 includes a communication circuit 232 and an antenna 234. In embodiments wherein the wireless communication device 230 is embodied as an RFID device (e.g., RFID device 500), the communication circuit 232 may be substantially similar to the communication device 502 illustrated in and described above in regard to FIG. 9. Additionally, the antenna 234 may be substantially similar to the antenna 504. Because the wireless communication device 230 is positioned on top of the acetabular cup 202 (i.e., on top of the rim surface 212), the device 230 may use higher frequencies to receive and/or transmit data compared to the embodiment illustrated in and discussed above in regard to FIGS. 1-4. For example, in one particular embodiment, the wireless communication device 230 is configured to transmit data, such as identification data associated with the orthopaedic implant 200 and/or implant sensor data, using a predetermined frequency in the very high frequency (VHF) or ultra high frequency (UHF) range. For example, the wireless communication device 230 may use a frequency in the range of about 30 megahertz to about 3,000 megahertz. In such embodiments, the antenna 34 may be embodied as a dipole antenna as illustrated in FIG. 6. The antenna 34 may be, for example, a straight line or a meandering line dipole antenna based on the desired frequency to be used by the wireless communication device 230. However, it should be appreciated that in other embodiments other types of antennas may be used.

Figure 8:
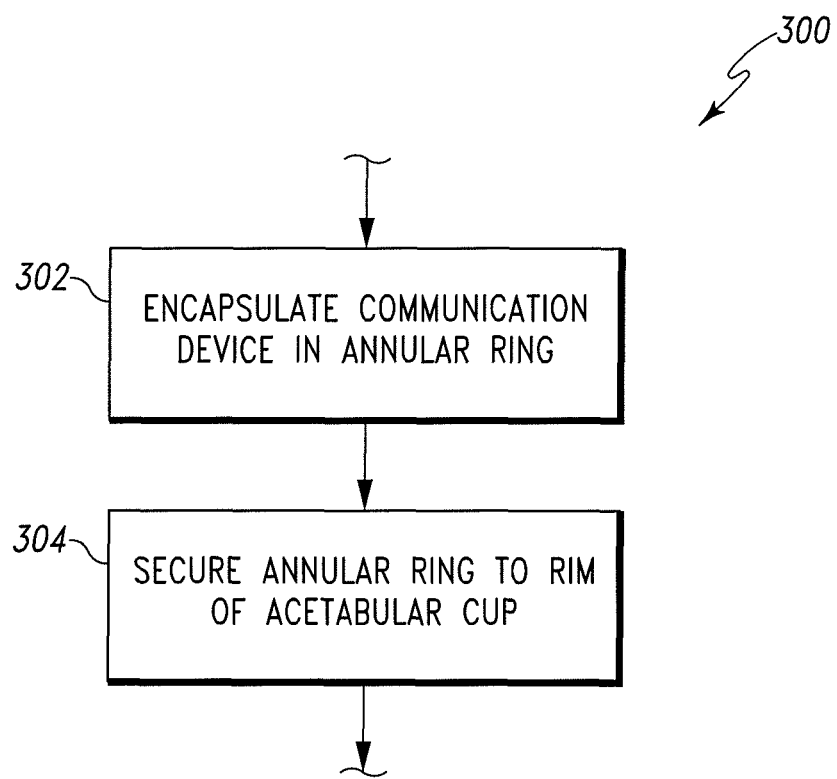
FIG. 8 is a simplified flowchart of an algorithm for fabricating the acetabular cup of the orthopaedic implant of FIG. 5.

Referring now to FIG. 8, an algorithm 300 for fabricating the orthopaedic implant 200 begins with a process step 302. In process step 302, the annular ring 220 is formed to include the wireless communication device 230. That is, the annular ring 220 is formed so as to encapsulate the wireless communication device 230. The wireless communication device 230 may be encapsulated by, for example, molding the annular ring 220 around the wireless communication device 230 in embodiments wherein the annular ring 220 is formed from a polymeric material such as polyethylene or ultra-high molecular weight polypropylene (UHMWPE). Alternatively, in some embodiments, the annular ring 220 may be formed to include an interior chamber. In such embodiments, the wireless communication device 230 may be positioned in the interior chamber of the annular ring 220 and subsequently sealed therein. Regardless, the wireless communication device 230 is encapsulated in or otherwise coupled to the annular ring 220 in process step 302.

Once the wireless communication device 230 has been encapsulated in the annular ring 220 in process step 302, the annular ring 220 is coupled to the acetabular cup 202 in process step 302. That is, the annular ring 220 is secured to the rim surface 212 of the acetabular cup 212. The annular ring 220 may be secured to the rim surface 212 using any suitable adhesive. For example, a biocompatible compound may be used such that the adhesive does not adversely affect the surrounding tissue or bone of the patient. Alternatively, in other embodiments, other types of securing devices and/or methods may be used to secure the annular ring 220 (and thereby the wireless communication device 230) to the rim surface 212 of the acetabular cup 202. For example, in some embodiments, a number of screws may be used to attach the annular ring 220 to the rim surface 212 of the acetabular cup 202. Alternatively, a snap slot may be milled or otherwise formed in the rim surface 212 of the acetabular cup 202 and the annular ring 220 may include a corresponding protrusion or lip formed on a bottom surface such that lip of the annular ring 220 mates (e.g., snaps into) the snap slot of the rim surface 212 to thereby secure the annular ring 220 to the acetabular cup 202.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems, apparatuses, and methods described herein. It will be noted that alternative embodiments of the systems and methods of the present disclosure may not include all of the features described yet still benefit from at least some of the advantages of such features. Those of ordinary skill in the art may readily devise their own implementations of the systems, apparatuses, and methods that incorporate one or more of the features of the present invention and fall within the spirit and scope of the present disclosure as defined by the appended claims.

The invention claimed is:

1. A method for fabricating an orthopaedic implant, the method comprising:
   forming an annular recess in a rim surface of an acetabular cup that is defined between an outer surface and an inner surface of the acetabular cup, the outer surface being configured to confront a portion of an acetabulum of a patient when the acetabular cup is implanted in the patient and the inner surface forming an inner cavity being configured to receive a bearing insert;
   positioning a wireless communication device in the annular recess; and
   securing the wireless communication device in the annular recess using a biocompatible compound.

2. The method of claim 1, wherein positioning a wireless communication device in the annular recess comprises positioning a radio frequency identification (RFID) tag in the recess.

3. The method of claim 1, wherein securing the wireless communication device in the annular recess comprises depositing an amount of bone cement in the recess.

4. The method of claim 1, wherein the inner surface of the acetabular cup has an annular outer edge, the outer surface of the acetabular cup has an annular outer edge, and the rim surface is substantially annular and planar and joins the annular outer edge of the inner surface to the annular outer edge of the outer surface.

5. The method of claim 4, wherein the annular recess in the rim surface has a substantially annular top profile.

\* \* \* \* \*